United States Patent
Waldvogel et al.

(10) Patent No.: US 12,366,002 B2
(45) Date of Patent: Jul. 22, 2025

(54) PROCESS FOR THE OXIDATION OF CARBON-CONTAINING ORGANIC COMPOUNDS WITH ELECTROCHEMICALLY GENERATED OXIDIZING AGENTS AND ARRANGEMENT FOR CARRYING OUT THE PROCESS

(71) Applicants: Condias GmbH, Itzehoe (DE); Johannes Gutenberg-Universität Mainz, Mainz (DE)

(72) Inventors: Siegfried Waldvogel, Gau-Algesheim (DE); Michael Zirbes, Mainz (DE); Rieke Neuber, Halstenbek (DE); Thorsten Matthée, Hohenaspe (DE)

(73) Assignees: Condas, GMBH, Itzehoe (DE); Johannes Gutenberg-Universität Mainz, Mainz (DE)

( * ) Notice: Subject to any disclaimer, the term of this patent is extended or adjusted under 35 U.S.C. 154(b) by 1014 days.

(21) Appl. No.: 17/292,612

(22) PCT Filed: Nov. 12, 2019

(86) PCT No.: PCT/EP2019/080918
§ 371 (c)(1),
(2) Date: May 10, 2021

(87) PCT Pub. No.: WO2020/099350
PCT Pub. Date: May 22, 2020

(65) Prior Publication Data
US 2022/0010443 A1    Jan. 13, 2022

(30) Foreign Application Priority Data
Nov. 12, 2018 (DE) ...................... 10 2018 128 228.1

(51) Int. Cl.
| | | |
|---|---|---|
| *C25B 11/061* | (2021.01) | |
| *C07C 45/29* | (2006.01) | |
| *C07D 301/12* | (2006.01) | |
| *C25B 1/30* | (2006.01) | |
| *C25B 9/17* | (2021.01) | |
| *C25B 9/67* | (2021.01) | |
| *C25B 11/052* | (2021.01) | |
| *C25B 11/059* | (2021.01) | |
| *C25B 11/063* | (2021.01) | |
| *C25B 11/065* | (2021.01) | |

(Continued)

(52) U.S. Cl.
CPC ............ *C25B 15/081* (2021.01); *C07C 45/29* (2013.01); *C07D 301/12* (2013.01); *C25B 1/30* (2013.01); *C25B 9/17* (2021.01); *C25B 9/67* (2021.01); *C25B 11/052* (2021.01); *C25B 11/059* (2021.01); *C25B 11/061* (2021.01); *C25B 11/065* (2021.01); *C25B 11/091* (2021.01); *C25B 15/021* (2021.01)

(58) Field of Classification Search
CPC ... C25B 15/081; C25B 15/021; C25B 11/061; C25B 11/059; C25B 11/052; C25B 11/02; C25B 11/063; C25B 11/091; C25B 9/17; C25B 9/67; C25B 1/30; C07C 45/29; C07D 301/12
See application file for complete search history.

(56) References Cited

U.S. PATENT DOCUMENTS

| | | | | |
|---|---|---|---|---|
| 5,747,658 A | * | 5/1998 | Veelaert | .................. C08B 31/18 536/18.5 |
| 10,030,087 B2 | * | 7/2018 | Chernysheva | ...... C08F 214/222 |

(Continued)

FOREIGN PATENT DOCUMENTS

| | | |
|---|---|---|
| CN | 104262395 A | 1/2015 |
| DE | 10 2011 078 468 A1 | 1/2013 |

(Continued)

OTHER PUBLICATIONS

Chardon et al., 2 ChemistrySelect 1037-1040 (2017) (Year: 2017).*

(Continued)

*Primary Examiner* — Timothy R Rozof
(74) *Attorney, Agent, or Firm* — WCF IP

(57) ABSTRACT

The invention relates to a process for the oxidation of carbon-containing organic compounds where the said compounds have at least one bond with a bond order >1, wherein an oxidizing of these carbon-containing organic compounds to be oxidized is performed with electrochemically generated C—O—O oxidizing agents, in particular peroxodicarbonate. Also described is the use of C—O—O oxidizing agents generated electrochemically from carbonate, in particular peroxodicarbonate, as oxidizing agents for the oxidation of carbon-containing organic compounds, in particular carbon-containing organic compounds where the said compounds have at least one bond with a bond order >1. Finally, an arrangement for the oxidation of carbon-containing organic compounds is provided, comprising a first unit for the electrochemical preparation of C—O—O oxidizing agents generated electrochemically from carbonate, in particular peroxodicarbonate, and a second unit for the oxidizing of the carbon-containing organic compound with the C—O—O oxidizing agent generated electrochemically from carbonate, in particular peroxodicarbonate. In this case, these two units are connected to one another in such a way that an ex situ generated oxidizing agent can be fed to the second unit.

4 Claims, No Drawings

(51) Int. Cl.
*C25B 11/091* (2021.01)
*C25B 15/021* (2021.01)
*C25B 15/08* (2006.01)

(56) References Cited

U.S. PATENT DOCUMENTS

2004/0074780 A1 4/2004 Twardowski et al.
2012/0253055 A1 10/2012 Ripplinger et al.

FOREIGN PATENT DOCUMENTS

DE 10 2016 113 727 A1 2/2018
RU 2181791 C2 4/2002

OTHER PUBLICATIONS

Dier et al: "Sustainable Electrochemical Depolymerization of Lignin in Reusable Ionic Liquids", Scientific Reports, vol. 7, No. 5041, Jul. 11, 2017.
Di Marino et al: "Electrochemical depolymerisation of lignin in a deep eutectic solvent", The Royal Society of Chemistry, vol. 18, pp. 6021-6028, 2016.
Fargues et al: Kinetics of Vanillin Oxidation, Chem. Eng. Technol., vol. 19, pp. 127-136, 1996.
Luo et al: "Selective Lignin Oxidation towards Vanillin in Phenol Media", Chemistry Select Communications, vol. 1, pp. 4596-4601, 2016.
Mathias et al: "Production of Vanillin by Oxidation of Pine Kraft Lignins with Oxygen", Holzforschung, vol. 49, No. 3, pp. 273-278, 1995.
Napoly et al: "H2O2-Mediated Kraft Lignin Oxidation with Readily Available Metal Salts: What about the Effect of Ultrasound?", Industrial & Engineering Chemistry Research, vol. 54, pp. 6046-6051, 2015.
Parpot et al: "Biomass conversion: attempted electrooxidation of lignin for vanillin production", Journal of Applied Electrochemistry, vol. 30, pp. 727-731, 2000.
Rinaldi et al: "Paving the Way for Lignin Valorisation: Recent Advances in Bioengineering, Biorefining and Catalysis", Angew. Chem. Int. Ed., vol. 55, pp. 8164-8215, 2016.
Schmitt et al: "Treatment of Black Liquor (BL) by adsorption on AE resins and a subsequent electrochemical degradation of BL to obtain vanillin", Holzforschung vol. 71, No. 1, pp. 35-41, 2017.
Silva et al: "An integrated process to produce vanillin and lignin-based polyurethanes for Kraft lignin", Chemical Engineering Research and Design, vol. 87, pp. 1276-1292, 2009.
Villar et al: "Oxidation of hardwood Kraft-Lignin to Phenolic Derivatices. Nitrobenzene and Copper Oxide as Oxidants", Journal of Wood Chemistry and Technology, vol. 17, No. 3, pp. 259-285, 1997.
Villar et al: "Oxidation of hardwood kraft-lignin to phenolic derivatives with oxygen as oxidant", Wood Science and Technology, vol. 35, pp. 245-255, 2001.
Voitl et al: "Oxidation of Lignin Using Aqueous Polyoxometalates in the Presence of Alcohols", Chemsuschem, vol. 1, pp. 763-769, 2008.
Wang et al: "Production of vanillin from lignin: The relationship between β-O-4 linkages and vanillin yield", Industrial Crops & Products, vol. 116, pp. 116-121, 2018.
Werhan et al: "Acidic oxidation of kraft lignin into aromatic monomers catalyzed by transition metal salts", Holzforschung, vol. 65, pp. 703-709, 2011.

\* cited by examiner

PROCESS FOR THE OXIDATION OF CARBON-CONTAINING ORGANIC COMPOUNDS WITH ELECTROCHEMICALLY GENERATED OXIDIZING AGENTS AND ARRANGEMENT FOR CARRYING OUT THE PROCESS

The invention relates to a process for the oxidation of carbon-containing organic compounds that have at least one bond with bond order ≥1, in which said compounds undergo oxidation to oxidized or oxygenated, carbon-containing organic compounds with electrochemically generated C—O—O oxidants, in particular peroxydicarbonate. Also described is the use of C—O—O oxidants generated electrochemically from carbonate, in particular peroxydicarbonate, as oxidants for the oxidation of carbon-containing organic compounds, in particular of carbon-containing organic compounds that have at least one bond with bond order 1. Finally, an assembly for the oxidation of carbon-containing organic compounds is provided, this comprising a first unit for the electrochemical production of C—O—O oxidants, in particular peroxydicarbonate, generated electrochemically from carbonate, and a second unit for the oxidation of the carbon-containing organic compound with the C—O—O oxidant, in particular peroxydicarbonate, generated electrochemically from carbonate. These two units are connected together in a manner that allows an ex-situ generated oxidant to be supplied to the second unit.

PRIOR ART

It has long been described that diamond electrodes, as a consequence of their high overvoltage, are able to bring about in-situ oxidization of water to ozone or hydrogen peroxide or formation of OH radicals. Diamond anodes have been used for example for the electrochemical production of oxidants such as persulfate, perphosphate, periodate, etc.

A process for the electrochemical production of peroxydicarbonate and accordingly configured electrochemical cells for the execution of this process have recently been described, see DE 10 2016 113 727 A1. Described therein is a process for the electrochemical production of peroxydicarbonate. This uses an electrolysis assembly comprising a cathode and a diamond-coated anode, carbonate-containing electrolytes; production takes place under defined reaction conditions. This was shown to be capable of providing peroxydicarbonate in good yield in appropriate concentrations.

The production of peroxydicarbonate from carbonate solutions by means of diamond anodes employed inter alia not only carbonate solutions obtained from sodium carbonate, but also potassium carbonate and mixtures thereof. As an alternative, the use of $CO_2$-saturated solutions is considered, which can be used for example with sodium hydroxide solution in the alkaline range.

The peroxydicarbonate thus produced is used in different ways. However, the use of peroxydicarbonate as oxidant is limited by its availability in suitable quantity, more specifically the supply of peroxydicarbonate in amounts suitable for industrial use. One possible means of providing peroxydicarbonate on an industrial scale, in which this is moreover present in acceptable concentrations, is described in DE 10 2016 113 727 A1.

Existing processes for the oxidation of organic compounds such as renewable raw materials have thus far been executed with oxidants using transition metals as catalysts. For example, processes for the oxidative depolymerization of kraft lignin as an example of renewable raw materials are described that are based on transition-metal-catalyzed reactions and/or use of nitrobenzene as oxidant. Such breakdown processes are however mostly nonselective. Moreover, the use of transition metal catalysts and/or toxic oxidants such as nitrobenzene, and also the toxic by-products obtained in such processes, necessitates particularly laborious and costly purification steps for the organic compounds thus oxidized. An example that may be described here is the production of vanillin from kraft lignin. Vanillin, which is used primarily in the fragrance, food, and cosmetic industries, needs to undergo laborious purification after oxidation of kraft lignin by transition metal catalysts or appropriate oxidants. Because of these drawbacks, industrial production is for environmental and economic reasons difficult to justify.

There is currently one process for the production of vanillin starting from lignin in which, as shown in Scheme 1, lignosulfonate undergoes base-catalyzed hydrolysis followed by copper-catalyzed oxidative depolymerization with oxygen.

Scheme 1
Oxidative breakdown of lignosulfonate to the flavor chemical vanillin.

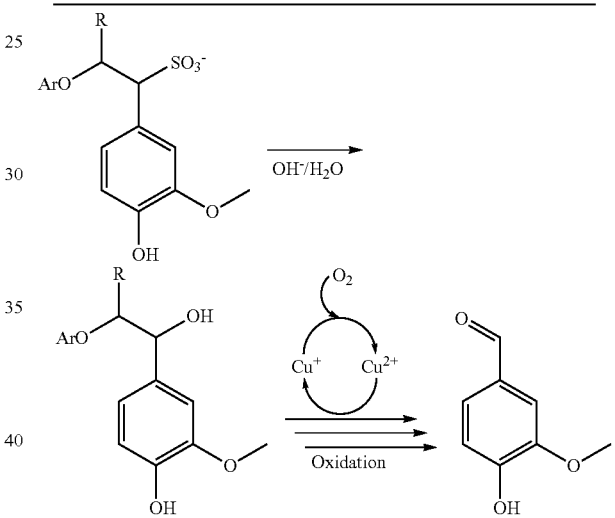

However, this synthesis route is associated with drastic reaction conditions. For example, a temperature of up to 170° C. and a pressure of up to 15 bar is applied. Moreover, the use of copper necessitates the use of additional costly ultrafiltration methods for purification of the product. Finally, it should be mentioned that the sulfite process for cellulose production, in which the requisite lignosulfonate is obtained, has been largely superseded by the kraft process. This is currently the almost exclusive means of sourcing, as a waste stream, the requisite kraft lignin (R. Rinaldi, R. et al., *Angew. Chem. Int. Ed.* 2016, 55, 8164-8215; *Angew. Chem.* 2016, 128, 8296-8354).

MATHIAS and RODRIGUES have reported the oxidative breakdown of kraft lignin using nitrobenzene as oxidant in alkaline media. This afforded vanillin in a maximum yield of 13% by weight. However, lignin breakdown was carried out at a temperature of approx. 150° C. for 7 h (A. L. Mathias, A. E. Rodrigues, *Holzforschung* 1995, 49, 273-278). In addition to the high input of energy, a special equipment setup is additionally required. The major drawback of this method is however the use of nitrobenzene, since this and the corresponding reduction products are toxic and carcinogenic.

Scheme 2 Oxidative breakdown of kraft lignin with nitrobenzene.

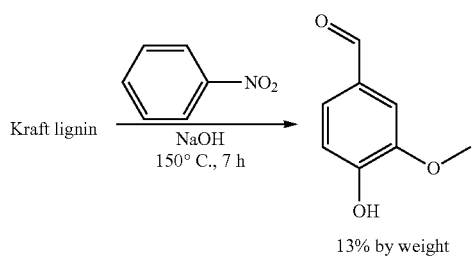

13% by weight

SUN and co-workers describe the breakdown of kraft lignin likewise using nitrobenzene as oxidant. At a temperature of 170° C. for 3 h, vanillin was obtained in a yield of 2.5% by weight. In addition to the drawbacks of depolymerization with toxic nitrobenzene described above, vanillin is obtained here in a markedly lower yield (Y. Wang et al., *Ind. Crops Prod.* 2018, 116, 116-121).

VILLAR et al. have published the oxidative breakdown of hardwood lignin obtained from black liquor. The use of nitrobenzene as oxidant afforded up to 14% by weight of phenolic aldehydes (mostly syringaldehyde and vanillin). In addition to the poor selectivity, the depolymerization was carried out under drastic reaction conditions (40 min, 190° C., 2 M NaOH), which are associated with high outlay on equipment and high safety requirements. However, the major drawback here too is the use of toxic nitrobenzene as oxidant. Moreover, obtaining the lignin used is associated with additional costly work steps (J. C. Villar, A. Caperos, F. García-Ochoa, *J. Wood Chem. Technol.* 1997, 17, 259-285).

Scheme 3
Breakdown of from hardwood lignin with nitrobenzene to phenolic aldehydes.

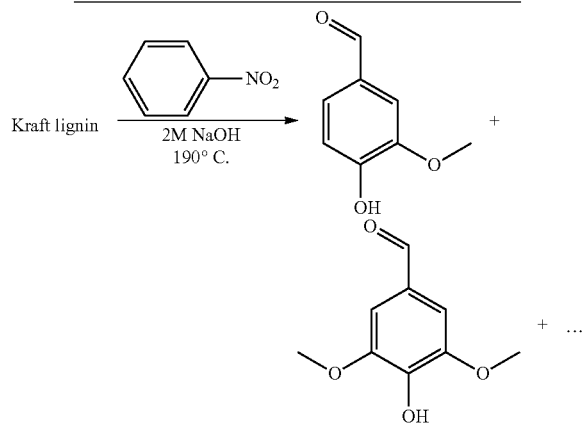

MATHIAS and FARGUES et al. have both reported the depolymerization of kraft lignin using oxygen as oxidant. The highest vanillin yield was 10% by weight, which was achieved at a temperature of 141° C. and an oxygen partial pressure of 4 bar (total pressure: 10 bar). However, the use of pure oxygen having a partial pressure of 4 bar is a safety concern and entails high outlay on equipment. This complicates industrial use and is associated with additional costs. Moreover, the vanillin yield, despite use of the same reaction conditions, is not achieved when a different kraft lignin from the same manufacturer is used. Thus, vanillin was obtained here in a maximum yield of only 4% by weight (Frargues. C. et al., *Chem. Eng. Technol.* 1996, 19, 127-136). The robustness and transferability of the reported breakdown method is this not assured.

ARAUJO has published the breakdown of kraft lignin using the previously described method. However, the vanillin yield amounted to less than 4% by weight. The breakdown reaction differed here solely in the kraft lignin used. Instead of *Pinus* SPP., INDULIN AT kraft lignin from the same manufacturer (WESTVACO) was used here. The considerable variation in the amount of vanillin obtained, alongside the disadvantages described above, thus casts further doubt on the comparability and transferability of the breakdown method (E. B. d. Silva et al., *Chem. Eng. Res. Des.* 2009, 87, 1276-1292).

VOITL and VON ROHR reported the oxidative breakdown of kraft lignin using polyoxometalates and oxygen in the presence of alcohols. They obtained the flavor chemical vanillin in a maximum yield of 1.2% by weight (T. Voitl, P. Rudolf von Rohr, *ChemSusChem* 2008, 1, 763-769).

Scheme 4 Breakdown of kraft lignin with a peroxometalate.

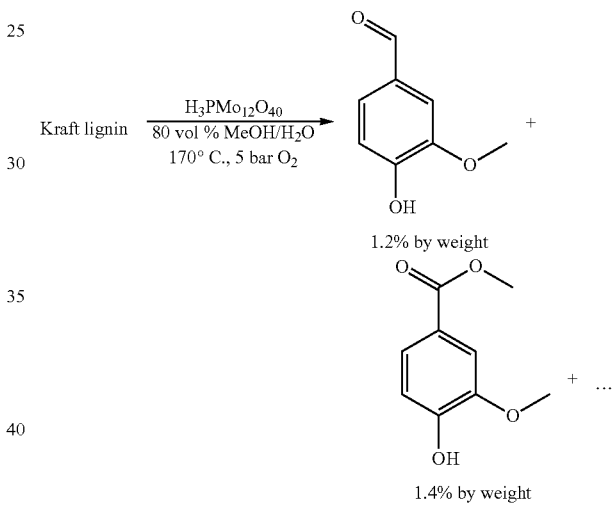

This oxidative depolymerization of kraft lignin affords not only vanillin, but also the overoxidation product methyl vanillate and other cleavage products. Thus, in addition to the low vanillin yield, this method also has low selectivity in respect of the flavor chemical. Moreover, the reaction parameters—a temperature of 170° C. and an oxygen partial pressure of 5 bar—place high demands on safety, which are associated with a high outlay on equipment. This is in turn reflected in high costs. The use of costly transition metal salts also necessitates additional costly purification steps. Finally, the low pH in this methodology complicates industrial use, since the lignin-containing waste stream from the cellulose industry has a high pH and thus a costly acidification would be necessary that would represent a further hindrance to the process cycle.

VON ROHR and co-workers also describe the depolymerization of kraft lignin with various transition metal salts. The use of $COCl_2$ and an oxygen partial pressure of 10 bar at 170° C. afforded vanillin in a maximum yield of 3.2% by weight. However, the use of carcinogenic Co(II) salts necessitates additional purification processes. Moreover, the maximum vanillin yield is relatively low (H. Werhan et al., *Holzforschung* 2011, 65, 703-709).

VILLAR et al. have investigated the depolymerization of eucalyptus kraft lignin using Cu(II) salts and Co(II) salts and oxygen. Under optimized conditions, vanillin was generated in a yield of approx. 1.2% by weight. However, the breakdown reaction was performed at a temperature of 170° C. and an oxygen partial pressure of 15 bar. However, these drastic reaction conditions again give rise to high safety requirements and necessitate a costly equipment setup. The use of CuO is moreover associated with additional purification measures. Finally, in addition to vanillin, overoxidation products such as vanillic acid are also observed, which must be removed from the product mixture (J. C. Villar, A. Caperos, F. García-Ochoa, *Wood Sci. Technol.* 2001, 35, 245-255).

Scheme 5 Depolymerization of kraft lignin using oxygen and CuO.

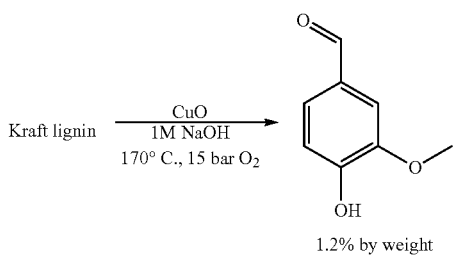

1.2% by weight

WALDVOGEL and co-workers have reported the electrochemical breakdown of kraft lignin on porous activated nickel foam anodes. Under mild reaction conditions at temperatures below 100° C., the flavor chemical vanillin is obtained in a yield of up to 1.7% by weight. However, this amount of vanillin could be achieved only through activation of the anode in black liquor, which industrially would be associated with a greater amount of work. Moreover, contamination of the electrolysis solution with nickel cannot be ruled out, which industrially would be associated with costly methods of purification (D. Schmitt et al., *Holzforschung* 2017, 71, 35-41).

Scheme 6
Electrochemical breakdown of kraft lignin on nickel foam electrodes.

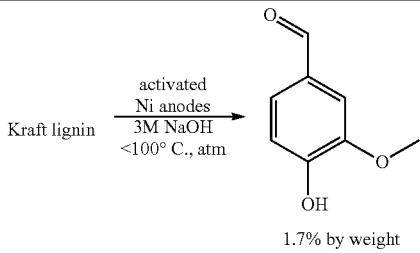

1.7% by weight

PAPOT et al. have published the electrochemical breakdown of kraft lignin using various anode materials (Pt, Au, Ni, Cu, DSA-$O_2$, and $PbO_2$). This study evaluated the production of vanillin. However, the vanillin yield never exceeded 10% by weight of the amount of kraft lignin used. Also, nothing was said about the selectivity of the depolymerization (P. Parpot, A. P. et al., *J. Appl. Electrochem.*, 2000, 30, 727-731). This methodology accordingly has little comparability.

HEMPELMANN and co-workers have demonstrated the oxidative breakdown of lignin using an electrode coated with a Ru—V—Ti mixed oxide. In addition, triethylammonium methanesulfonate was used as an ionic liquid. However, a complex product mixture of aromatic compounds was detected by GC-MS, HPLC, and HRMS. Moreover, significant amounts of water are needed to remove the ionic liquid. This method is thus, primarily from an economic viewpoint, industrially unworkable (T. K. F. Dier et al., *Sci. Rep.* 2017, 7, 5041).

DRAYE et al. have reported the oxidative breakdown of kraft lignin promoted by sonication. The use of $H_2O_2$ and $Na_2WO_4.2H_2O$ as catalyst afforded vanillin, acetylvanillin, guaiacol, and vanillic acid in an overall yield of 0.5% by weight. The breakdown reaction is however nonselective and affords vanillin in only very low yield (F. Napoly et al., *Ind. Eng. Chem. Res.* 2015, 54, 6046-6051).

WESSLING and co-workers have published the electrochemical depolymerization of kraft lignin in deep eutectic solvents. Vanillin and guaiacol were identified as principal components by GC-MS. However, no quantification of cleavage products, optimization of the electrolysis, or recycling of the deep eutectic solvents was carried out. This study accordingly has low information value (D. Di Marino et al., *Green Chem.* 2016, 18, 6021-6028).

LUO et al. describe the oxidative depolymerization of kraft lignin using $Al_2O_3$-supported $ReO_x$ nanoparticles and oxygen. Using harsh reaction parameters (120° C., 2 bar $O_2$), vanillin was obtained in a GC yield of max. 7.4% by weight. In addition to using nanoparticles that are laborious to produce, toxic phenol was also used as solvent. These components must in addition be laboriously removed from the product mixture (J. Luo et al., *Chemistry Select* 2016, 1, 4596-4601).

Scheme 7
Depolymerization of kraft lignin using $ReO_x/\gamma$-$Al_2O_3$ nanoparticles.

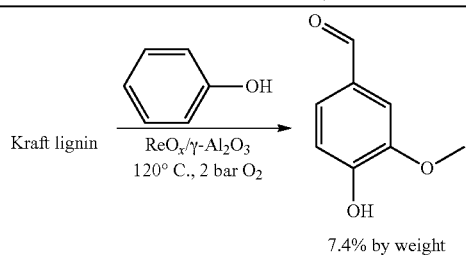

7.4% by weight

In all cases it was found that oxidation of kraft lignin results only in a low yield of vanillin.

An oxidation of carbon-containing organic compounds is often carried out in chemistry. In the preparation of epoxides, for example direct epoxidation of organic compounds that have a bond with bond order >1, e.g. of aromatics or other organic compounds having a double bond, an oxidation often takes place.

DESCRIPTION OF THE INVENTION

The object of the present invention is accordingly to provide a process for the oxidation of carbon-containing organic compounds that—after factoring in economic and environmental considerations—can be executed on an industrial scale and in which the yield, e.g. of the end product vanillin, is possible in adequate concentration.

To achieve this object, a process of the type mentioned in the introduction is according to the invention characterized in that the oxidation of the carbon-containing organic compounds is carried out with electrochemically generated C—O—O oxidants, in particular peroxydicarbonate. The invention is based on the finding that the electrochemically generated C—O—O oxidant, in particular peroxydicarbonate, can be provided selectively, inexpensively, and in an environmentally friendly manner. It was found that both lignin as an example of a renewable organic raw material and direct epoxidation of e.g. aromatics or enones is generally possible.

It is possible for electrochemically generated C—O—O oxidants to be generated in considerably increased yield and thus in increased concentration, allowing them to be used inexpensively and in an environmentally friendly manner. These C—O—O oxidants comprise in particular peroxydicarbonate. In one embodiment the oxidant is peroxydicarbonate. This makes it possible to avoid using costly and/or toxic transition metals, catalysts or other toxic oxidants such as nitrobenzene. The process of the invention has not only economic, but in particular also environmental advantages.

The expression "C—O—O" oxidant is understood as meaning a compound that has a peroxy "—O—O" group. In other words, the C—O—O group is here a peroxydicarbonate group.

The organic compound is here one that has at least one bond with a bond order of ≥1, such as a bond order of 1, 1.5, 2, 2.5 or 3.

It has surprisingly also been found that, e.g. in the case of kraft lignin, a high selectivity and good yield of vanillin after depolymerization of the kraft lignin is possible.

The process of the invention enables for the first time the use of electrochemically generated C—O—O oxidants, in particular peroxydicarbonate, for the selective oxidation of carbon-containing organic compounds, shown by way of example for kraft lignin, and for the direct epoxidation of organic compounds.

Scheme 8 illustrates, taking kraft lignin as an example, the oxidation using peroxydicarbonate produced electrochemically according to the invention.

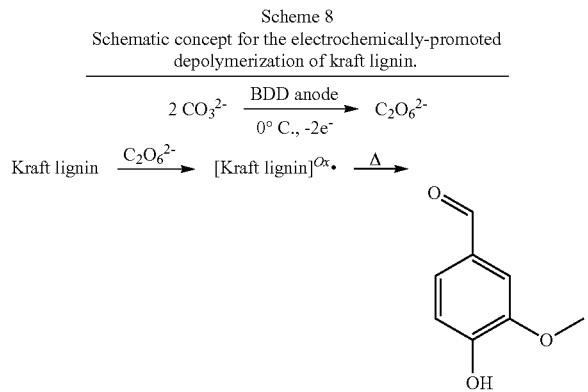

Scheme 8
Schematic concept for the electrochemically-promoted depolymerization of kraft lignin.

In one embodiment, the process of the invention is a process in which the C—O—O oxidant, in particular peroxydicarbonate, generated electrochemically from carbonate, of one is obtained with a process for the electrochemical production thereof, by means of an electrolysis assembly that includes at least one cathode, at least one diamond-coated anode, and a carbonate-containing electrolyte that is pumped at a flow rate through an electrolyte chamber between the anode and cathode, wherein the carbonate concentration in the carbonate-containing electrolyte is set at ≥0.5 M, the current density between the anode and cathode is set at ≥0.1 A/cm², such as ≥0.5 A/cm², and that a pressure of ≥1 bar, such as ≥2 bar, is generated in the electrolysis assembly, and the electrolyte is optionally cooled to below room temperature.

In one embodiment, the current density can be at least 0.1 A/cm², such as at least 0.2 A/cm², such as 0.3 A/cm², in particular such as ≥0.5 A/cm². The current density can in one embodiment be ≥1 A/cm², in particular ≥1.4 A/cm².

The electrolysis assembly here has a pressure of 1 bar, such as 2 bar, such as ≥3 bar, in particular ≥4 bar. The process pressure in the electrolysis assembly is set accordingly. Increasing the process pressure to higher overpressures of for example up to 20 bar is possible, this necessitating an appropriate construction for the electrolysis cell.

In one embodiment, the carbonate is present at least in the anolyte.

At higher current densities, increased gas evolution can develop at the anode, which can occur as a consequence of a local change in pH at the anode, wherein carbonate is discharged in the form of carbon dioxide gas. In one embodiment, a gas-diffusion electrode (GDE) can accordingly be used, in which either H₂ production is suppressed or the generation of oxidative oxygen species such as H₂O₂ takes place, this potentially promoting the formation of e.g. peroxydicarbonate. To further prevent CO₂ from being discharged or H₂ gas from being driven out, it is possible to use pressure-based electrolytes. The electrolyte pressures are therewith kept as similar as possible, the optimal pressure for the synthesis being easily determined.

In one embodiment, the anode used is a boron-doped diamond anode, as mentioned described for example in DE 10 2016 113 727 A1 or in EP1036861A1.

The process of the invention for the oxidation of carbon-containing organic compounds is in one embodiment one that oxidizes organic compounds having an aryl group, a heteroaryl group, a vinyl group, such as an allyl group, or in a benzylic position. These organic compounds also include enones, i.e. ketones that additionally contain a C=C double bond.

In one embodiment, the process is one in which the C—O—O oxidant is generated electrochemically. The carbonate-containing electrolytes used comprise a carbonate salt, for example at least two types of carbonate salt having inorganic or organic cations, in particular two different alkali metal carbonates. Organic carbonate salts include those with tetraalkylammonium and guanidinium.

By using at least two types of carbonate, that is to say two carbonate salts, such as in particular two different alkali metal carbonate salts, it is possible to obtain large amounts of peroxydicarbonate in the electrolyte.

It has surprisingly been found that, when using electrolytes based on mixed carbonate salts, in particular alkali metal carbonates, for example a mixture of sodium carbonate and potassium carbonate, the concentration of peroxydicarbonate in the electrolyte increases, allowing peroxydicarbonate accordingly to be obtained in high concentrations. In one embodiment of the present invention, the electrochemically produced peroxydicarbonate is therefore one that in the electrolyte in a concentration of at least with a molar amount of 0.02 mmol/ml, such as 0.1 mmol/ml, for example greater than 0.3 mmol/ml.

Optimal temperatures for the generation of the C—O—O oxidant, and of peroxydicarbonate in particular, are 0° C., that is to say the electrolyte is cooled to below room temperature, in particular to below 10° C., such as to below 0° C. The electrolysis assembly is configured accordingly.

In one embodiment, the process of the invention for the oxidation of carbon-containing organic compounds is one in which the oxidized carbon-containing organic compounds obtained have at least one epoxy group. The process can generally be used for the oxidation of carbon-containing organic compounds, in particular for the epoxidation of such compounds.

In another embodiment, the process of the invention is suitable in particular for the oxidization of renewable raw materials such as lignin, for example kraft lignin, in a subsequent depolymerization process such as is shown for example in Scheme 8, the flavor compound vanillin can then be obtained in high yield. This was unexpected, since the use of other oxidants such as $H_2O_2$ or percarbonate for this synthesis of vanillin is not possible in an efficient manner.

The C—O—O oxidants generated electrochemically from carbonates, in particular peroxydicarbonate, may contain stabilizing additives. The stability of these oxidants, and of peroxydicarbonate in particular, can be enhanced by reducing the temperature, since this lowers the rate of decomposition of e.g. peroxydicarbonate. An increased concentration of the oxidant can likewise be achieved through a high current density.

For further stabilization, the generated C—O—O oxidant, in particular peroxydicarbonate, may include the mentioned stabilizing additives. Stabilizing additives here include phosphorus-based additives or silicate-based or boron-based additives. Other stabilization options involve process-related measures such as lowering the temperature and/or crystallizing with or without isolation of the peroxydicarbonate.

In one embodiment, the electrochemical generation takes place in an electrolysis assembly and the oxidation of the carbon-containing organic compounds takes place spatially separated therefrom, in a further reaction space.

The expression "spatially separated" is in the present case understood as meaning that the oxidation takes place separately from the generation of the peroxy compound. The individual reaction zones are locally/spatially separated. These spatially separated zones may be present within a single apparatus or in various apparatuses, with supply effected for example via a feed line carrying the peroxy oxidant to the site of the oxidation reaction.

In one embodiment of the present invention, the electrochemical generation of the C—O—O oxidant, in particular peroxydicarbonate, takes place ex situ alongside the unit, an apparatus, for example in the form of a reactor, for the oxidation of the carbon-containing organic compounds. In one embodiment, the C—O—O oxidant generated ex situ, in particular peroxydicarbonate, is accordingly fed into the oxidation apparatus; in another embodiment, the temperature of the solution containing the oxidant, such as peroxydicarbonate, is thereafter altered, e.g. increased. Appropriate regulation of the temperatures is possible and appropriate temperature programs may be executed. For example, the production of the oxidant takes place at a first temperature, the oxidation at a second temperature that can be higher, the same or lower and with a further reaction optionally taking place at a third temperature, for example a high temperature for the depolymerization in the case of production of vanilla from lignin. The C—O—O oxidant, in particular peroxydicarbonate, can be supplied in directly as the electrolyte solution from the oxidation of the carbon-containing organic compound. Interim storage can optionally take place, in particular with the use of stabilizing additives.

A correspondingly adjusted heat supply to the components is possible. That is to say, it is possible according to the invention for ex-situ generation of the C—O—O oxidant, and of peroxydicarbonate in particular, to take place at temperatures below room temperature, such as at below 10° C., in particular below 0° C., so as then to supply the resulting electrolyte to the apparatus for the oxidation of the carbon-containing organic compounds alongside an increase in temperature. The increase or decrease can take place in two or more stages. Lowering the temperature to stabilize the oxidant can additionally be carried out.

In one embodiment, the electrolysis assembly may be a flow-through electrolysis cell, preferably a divided cell, more preferably one in which the catholyte is likewise a carbonate. In the divided cell, the anolyte and catholyte have less effect on one another. In a divided cell, reductive processes that have been shown to be economically viable can take place in the catholyte at the same time. In one embodiment, the catholyte can likewise comprise carbonate.

In one embodiment, the diamond electrode is one having an $sp^3$ diamond layer that is as pure as possible, with low contamination an $sp^2$ carbon species, e.g. one exhibiting a specific resistance of 2 mOhm-cm≥100 mOhm-cm≥1000 mOhm-cm.

A further aspect discloses the use of electrochemically generated C—O—O oxidants, in particular peroxydicarbonate, as oxidants for the oxidation of carbon-containing organic compounds, in particular of carbon-containing organic compounds that have at least one bond order ≥1. It has surprisingly been shown that the oxidant generated electrochemically from carbonate described herein, such as peroxydicarbonate, caused oxidation, for example epoxidation, of such organic compounds. This constitutes an inexpensive and environmentally valuable alternative to the use of costly or toxic transition metal catalysts or other chemical oxidants.

In one embodiment, the use of C—O—O oxidants such as peroxydicarbonate is disclosed, the carbon-containing organic compounds being selected from those having an aryl group, those having a heteroaryl group, those having a vinyl group, such as an allyl group, enones, etc., in particular for the epoxidation of said organic compounds.

The use of said C—O—O oxidants, in particular peroxydicarbonate, for the oxidation of renewable raw materials including lignin, such as kraft lignin, is alternatively described.

In one embodiment, the use according to the invention involves the electrochemical generation, in an ex-situ process, of the C—O—O oxidant, such as peroxydicarbonate, this then being fed into the apparatus for the oxidation of the carbon-containing organic compounds, such as into an appropriate reactor.

In a further aspect, the present invention to an assembly for the oxidation of carbon-containing organic compounds, said assembly comprising a first unit for the electrochemical production of C—O—O oxidants, in particular peroxydicarbonate, generated electrochemically from carbonate, by means of an electrolysis assembly, and a second unit for the oxidation of carbon-containing organic compounds with C—O—O oxidants, in particular peroxydicarbonate, generated electrochemically from carbonate, wherein the unit for the production of C—O—O oxidant, in particular peroxydicarbonate, generated electrochemically from carbonate is connected by a conduit to the unit for the oxidation of carbon-containing organic compounds with C—O—O oxidants, in particular peroxydicarbonate, generated electrochemically from carbonate, for the supply of the C—O—O oxidant, in particular peroxydicarbonate, produced electrochemically from carbonate in the first unit. These two units are in particular present with spatial separation.

The first unit may be one as for example in DE 10 2016 113 727 A1. The second unit is a standard unit, such as a reactor, for the reaction of organic compounds with oxidants. It is appropriately furnished with fittings resistant to such oxidants and to the organic compounds including the necessary solvents.

The first unit and the second unit are according to the invention connected to one another by a conduit. That is to say, the C—O—O oxidant, in particular peroxydicarbonate, generated in the electrolysis assembly is supplied—or stored temporarily—directly to the second unit, with the conveyance of this oxidant, e.g. of the oxidant present in the withdrawn electrolyte solution, optionally accompanied by a temperature change, in particular a heating of the solution. Accordingly present in one embodiment of the assembly according to the invention is additionally a unit for temperature regulation, in particular a unit for controlling the temperature of the first unit and of the second unit and of the connecting supply line. Whereas in the first unit, the electrolysis assembly, preference is given to cooling, as described above, the temperature in the second unit for the oxidation may be increased, the same, or decreased.

In another embodiment of the assembly according to the invention, the unit for the production of C—O—O oxidants, such as peroxydicarbonate, is one where the electrolysis assembly is one that has at least one diamond-coated anode, in particular a boron-doped diamond-coated anode, a pump for pumping a carbonate-containing electrolyte at a flow rate through an electrolyte chamber, and a device for generating a pressure of at least 1 bar, such as at least 2 bar.

In one embodiment, the electrolysis assembly is an electrochemical cell having a flat cathode element, preferably made of a metal, an anode that toward the cathode has a doped diamond coating on a metallic, Si-based or graphitic substrate, in particular a boron-doped diamond coating, a seal that bounds an electrolyte chamber between cathode and anode in the form of a frame, said seal being pressed against the cathode and the anode by means of a contact-pressure device, and a cooling unit on the electrochemical cell for cooling the electrolyte chamber, such as a flat cooling element arranged side of the anode facing away from the cathode for cooling the anode by means of a coolant flowing in a coolant chamber formed between the anode and the cooling element.

In addition, the assembly can in one embodiment be one in which the electrochemical cell in the cathode element has a flow chamber designed for the electrolyte that is furnished with inflow channels and outflow channels to the electrolyte chamber, which are arranged at different ends of the electrolyte chamber to form a direction of flow.

In another embodiment, the electrochemical cell is one in which the cooling element is designed with a flow chamber for the coolant that is furnished with inflow channels and outflow channels to a sealed coolant chamber adjoining the anode, the inflow channels and outflow channels being arranged at different ends of the coolant chamber to form a direction of flow.

The assembly of the invention additionally includes in one embodiment an apparatus for regulating the current density, the pressure, the through-flow, and the carbonate concentration in the electrolyte.

The process of the invention allows an oxidation of carbon-containing organic compound to be carried out easily and highly effectively. The oxidant used is characterized not only by high environmental friendliness, but especially also by cost-efficient and easy production. It is possible to produce relatively large amounts of oxidant without high synthetic outlay. Reagent waste, in particular toxic waste, are avoided.

A change in pH to an acid level of not higher than pH 4, such as pH 1, below pH 1, such as pH 0, causes $CO_2$ to be driven off. On the one hand, this simplifies the subsequent disposal of the electrolyte. Alternatively, it is for example possible to install a recycling process for reactants such as lignin and $CO_2$ for the generation of carbonate.

The C—O—O oxidant, in particular peroxydicarbonate, thus obtained shows high selectivity not only e.g. in the synthesis of vanillin from lignin, but also in the epoxidation of organic compounds.

The present invention is elucidated in more detail with reference to examples, but without being limited thereto.

1. Production of Peroxydicarbonate from Mixed Carbonates

The low solubility of sodium carbonate in water at low temperatures (7.1 g $Na_2CO_3$ in 100 g $H_2O$ at 0° C.) is a limiting factor for peroxydicarbonate (PODIC) synthesis. Sodium carbonate solutions with concentrations above 1 M are scarcely achievable at temperatures of 0° C. This means that, under these reaction conditions, the electrochemically generated oxidant is unable to achieve a concentration of higher than 500 mM. To increase the maximum (absolute) concentration of PODIC, a mixture of sodium and potassium carbonate was however used. This allowed the total concentration of carbonate to be increased. Using a mixed carbonate solution consisting of 1 M $Na_2CO_3$ and 1.25 M $K_2CO_3$, it was possible to increase the absolute amount of PODIC (electrolysis of 1 M $Na_2CO_3$ solution: 185 mM PODIC; electrolysis of 1 M $Na_2CO_3$/1.25 M $K_2CO_3$ solution: 229 mM PODIC). The electrochemical synthesis of the mixed PODIC is carried out according to general work procedure 1. This is done by electrolyzing 35 ml of an aqueous 1 M $NaCO_3$/1.25 M $K_2CO_3$ carbonate solution at 0° C. using a charge amount of 7598 C (1 F), a current density of 240 mA/cm$^2$, and a flow rate of 50 ml/min.

The electrochemical synthesis of PODIC is carried out in a flow-through electrolysis cell. This consists of a Teflon half into which a 12 cm$^2$ boron-doped diamond electrode (anode) is introduced. The second half is a thermostatically-controllable stainless steel block that simultaneously serves as the cathode. The two halves of the cell are separated from one another by a Teflon seal (thickness: 1 mm) and can be screwed together from the outside. The continuous electrolysis was carried out undivided. The flow-through electrolysis was moreover operated in a circulation process in which the electrolyzed reaction mixture was fed back into the starting solution at a constant flow rate.

35 ml of the appropriate aqueous carbonate solution is transferred to a 100 ml vessel and cooled to 0° C. This solution is then electrolyzed with ice-cooling in a circulation process by means of the flow-through electrolysis unit described above. Serving as the anode is a boron-doped diamond (A=12 cm$^2$) and as the cathode a stainless steel block (A=12 cm$^2$) that is likewise cooled to 0° C. The applied charge amount, current density, and flow rate can be varied. At the end of the electrolysis the entire reaction mixture is, by means of the pump, completely transferred back into the vessel and can be reused.

2. Conversion of Kraft Lignin into Vanillin by the Process of the Invention

The electrochemical synthesis of PODIC is carried out as described above. For this, 35 ml of an aqueous carbonate solution is reacted using the optimized electrolysis parameters. For the electrolysis of the 1 M $Na_2CO_3$ solution, a charge amount of 6754 C (2 F), a current density of 240 $mA/cm^2$, and a flow rate of 50 ml/min is applied. The PODIC solution generated is added to an alkaline kraft lignin solution (200 mg kraft lignin in 100 g of 3 M NaOH) heated to 50° C. The reaction mixture is then heated with stirring in a Teflon-coated pressure cell for 5 h at 180° C. At the end of the reaction, the solution is acidified to pH 2 with concentrated HCl (approx. 30 ml) and extracted with several portions of ethyl acetate. The combined organic phase is dried over $MgSO_4$ and the solvent removed by distillation under reduced pressure. Purification by column chromatography (cyclohexane/ethyl acetate=2:1) affords respectively vanillin and acetylvanillin.

3. Direct Epoxidation of Alkene with PODIC

The electrochemical synthesis of PODIC is carried out as described above. For this, 35 ml of an aqueous carbonate solution is reacted using the optimized electrolysis parameters. For the electrolysis of the 1 M $Na_2CO_3$ solution, a charge amount of 6754 C (2 F), a current density of 240 $mA/cm^2$, and a flow rate of 50 ml/min is applied. At the end of the reaction, the appropriate amount of peroxydicarbonate required is withdrawn using a graduated pipette. The respective substrate (alkene) is added to 100 ml of solvent (ethanol or methanol) and brought into solution, with stirring, at room temperature. To the mixture is then added the appropriate amount of peroxydicarbonate solution with strong convection at room temperature or 0° C. The progress of the reaction can be monitored by gas chromatography. At the end of the reaction, the reaction mixture is treated with 100 ml of water and extracted with three 100 ml portions of ethyl acetate. The combined organic phase is dried over magnesium sulfate and the solvent removed by distillation under reduced pressure. The residue obtained is then characterized by NMR spectroscopy.

2,3-Dihydro-2,3-epoxy-2-methyl-1,4-naphthoquinone

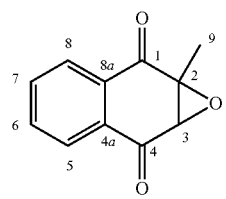

The epoxidation reaction is carried out as described. The reaction of 344 mg (2.0 mmol) of 2-methyl-1,4-naphthoquinone in 100 ml of ethanol with 2.4 mmol of $Na_2C_2O_6$ in 13 ml of electrolyzed carbonate solution affords 362 mg (1.9 mmol, 95%) of the epoxide as a light beige solid.

M.p.: 95-96° C. (ethyl acetate); (lit. 95-98° C.)

$^1$H NMR (300 MHz, $CDCl_3$): δ=1.76 (s, 3H, H-11); 3.88 (s, 1H, H-3); 7.70-7.84 (m, 2H, H-6, H-7); 7.91-8.11 (m, 2H, H-5, H-8) ppm.

$^{13}$C NMR (75 MHz, $CDCl_3$): δ=14.7 (C-9); 61.34 (C-3); 61.5 (C-4); 126.8 (C-6); 127.5 (C-7); 132.0 (C-5); 132.1 (C-8); 134.4 (C-8a); 134.6 (C-4a); 191.8 (C-1); 191.9 (C-4) ppm.

The analytical data match the literature data.

2,3-Dihydro-2,3-epoxy-1,4-naphthoquinone

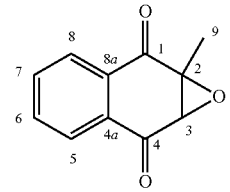

The epoxidation reaction was carried out as described. 325 mg (2.1 mmol) of 1,4-naphthoquinone is dissolved in 100 ml of ethanol and treated at 0° C. with 3.1 mmol of $Na_2C_2O_6$ in 16.8 ml of electrolyzed carbonate solution. After a reaction time of 30 min, workup affords 285 mg (1.7 mmol, 81%) of the epoxide as a pale reddish solid.

M.p.: 120-122° C. (ethyl acetate); (lit. 125° C.)

$^1$H NMR (300 MHz, $CDCl_3$): δ=4.02 (s, 2H, H-2, H-3); 7.73-7.81 (m, 2H, H-6, H-7); 7.95-8.03 (m, 2H, H-5, H-8) ppm.

$^{13}$C NMR (75 MHz, $CDCl_3$): δ=55.3 (C-2, C-3); 127.2 (C-5, C-8); 131.8 (C-6, C-7); 134.7 (C-8a, C-4a); 190.7 (C-1, C-6) ppm.

The analytical data match the literature data.

2,3-Epoxy-3,5,5-trimethylcyclohexan-1-one

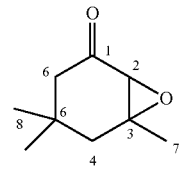

The epoxidation reaction was carried out as described. 285 mg (2.0 mmol) of isophorone is dissolved in 100 ml of ethanol and to this is added at room temperature, over a period of 120 h, 71 mmol of $Na_2C_2O_6$ in 385.0 ml of electrolyzed carbonate solution. Workup affords 181 mg of crude product as a colorless liquid. The quantity of the epoxide is calculated from the integrals in the NMR spectrum. This showed a yield of 165 mg (1.1 mmol, 55%) of the epoxide. The integrals in the $^1$H and $^{13}$C NMR spectra were assigned in accordance with the literature. The starting material isophorone is obtained as a side product.

$^1$H NMR (300 MHz, $CDCl_3$): δ=0.91 (s, 3H, H-8); 1.01 (s, 3H, H-8); 1.42 (s, 3H, H-7); 1.65-1.84 (m, 2H, H-4); 2.03-2.11 (m, 1H, H-6); 2.62 (dd, $^2J$=13.2 Hz, $^4J$=0.9 Hz, 1H, H-6); 3.05 (s, 1H, H-2) ppm.

$^{13}$C NMR (75 MHz, CDCl$_3$): δ=24.1 (C-8); 27.9 (C-8); 30.9 (C-7); 36.2 (C-5); 42.8 (C-4); 48.0 (C-6); 61.5 (C-3); 63.4 (C-2); 208.1 (C-1) ppm.

The analytical data match the literature data.

1,3-Diphenyl-2,3-epoxypropan-1-one

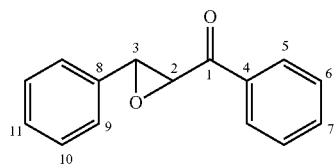 [SMILES: O=C(c1ccccc1)C1OC1c1ccccc1]

The epoxidation reaction was carried out as described. For this, 351 mg (1.7 mmol) of chalcone is dissolved in 100 ml of ethanol and treated at room temperature with 12.9 mmol of Na$_2$C$_2$O$_6$ in 35.0 ml of electrolyzed carbonate solution. After a reaction time of one hour, subsequent workup affords 345 mg (1.5 mmol, 88%) of the epoxide as a colorless solid.

M.p.: 86-88° C. (ethyl acetate); (lit. 86-88° C.)

$^1$H NMR (300 MHz, CDCl$_3$): δ=4.08 (d, $^3$J=1.9 Hz, 1H, H-3); 4.31 (d, $^3$J=1.9 Hz, 1H, H-2); 7.35-7.44 (m, 5H, H-9, H-10, H-11); 7.46-7.53 (m, 2H, H-6); 7.59-7.66 (m, 1H, H-7); 7.97-8.05 (m, 2H, H-7) ppm.

$^{13}$C NMR (75 MHz, CDCl$_3$): δ=59.1 (C-3); 60.7 (C-2); 125.5 (C-aromatic); 128.1 (C-aromatic); 128.5 (C-aromatic); 128.6 (C-aromatic); 128.8 (C-aromatic); 133.7 (C-8); 135.2 (C-4); 192.8 (C-1) ppm.

The analytical data match the literature data.

Solvents suitable for performing the oxidation are known to those skilled in the art; these include in particular aqueous and/or alkaline media. In the case of e.g. lignin, the appropriate solvents and the media used should be aqueous and/or alkaline media.

The reaction conditions are adjusted according to the carbon-containing organic compounds to be oxidized. This usually involves varying the temperature of the system. Suitable reaction conditions are known to those skilled in the art.

The invention claimed is:

1. An assembly for the oxidation of carbon-containing organic compounds, comprising:
    a first unit for the electrochemical production of dioxodicarbonate oxidant from at least one carbonate, wherein the dioxodicarbonate oxidant is generated electrochemically using an electrolysis assembly, and
    a second unit which is spatially separated from the first unit for the oxidation of carbon-containing organic compounds selected from the group consisting of lignin,
    carbon-containing compounds having an acyl group,
    carbon-containing compounds having a heteroaryl group, and
    carbon-containing compounds having a vinyl group,
    a conduit which connects the first unit to the second unit for the supply of dioxodicarbonate oxidant produced electrochemically from the carbonate in the first unit to the second unit, and
    a temperature regulation unit which regulates a temperature of the first unit to 10° C. or below, and regulates a temperature of the second unit to a temperature that is higher than in the first unit.

2. An assembly as claimed in claim 1 for the oxidation of carbon-containing organic compounds, wherein the first unit comprises at least one cathode, at least one diamond-coated anode, a pump for pumping a carbonate-containing electrolyte at a flow rate through an electrolyte chamber, and a device for generating a pressure of at least 1 bar.

3. An assembly as claimed in claim 1, wherein the electrolysis assembly is an electrochemical cell having
    a flat cathode element,
    an anode that toward the cathode has a doped diamond coating on a metallic or Si-based or graphitic substrate,
    a seal that bounds an electrolyte chamber between the cathode and the anode in a form of a frame, wherein said seal is pressed against the cathode and the anode by a contact-pressure device, and
    a flat cooling element arranged on a side of the anode facing away from the cathode for cooling the anode by a coolant flowing in a coolant chamber formed between the anode and the cooling element.

4. An assembly as claimed in claim 1 further comprising an apparatus for regulating current density, pressure, through-flow, and/or carbonate concentration in an electrolyte.

\* \* \* \* \*